United States Patent [19]

Franek et al.

[11] Patent Number: 4,881,897
[45] Date of Patent: Nov. 21, 1989

[54] TOOTH-ROOT IMPLANT WITH LONG-TERM RESISTANCE TO REPETITIVE STRESSES

[75] Inventors: Henning Franek, Braunfels; Klaus-Konrad Deutscher, deceased, late of Wetzlar, by Anneliese Deutscher, executor; Heinz Broemer, Wetzlar; Volker Strunz, Berlin; Wolfgang Rosenkranz, Schoeffengrund-Niederquembach, all of Fed. Rep. of Germany

[73] Assignee: Ernst Leitz Wetzlar GmbH, Wetzlar, Fed. Rep. of Germany

[21] Appl. No.: 154,349
[22] PCT Filed: May 7, 1987
[86] PCT No.: PCT/DE87/00206
§ 371 Date: Jan. 7, 1988
§ 102(e) Date: Jan. 7, 1988
[87] PCT Pub. No.: WO87/06816
PCT Pub. Date: Nov. 19, 1987

[30] Foreign Application Priority Data
May 9, 1986 [DE] Fed. Rep. of Germany ....... 3615733

[51] Int. Cl.⁴ .............................................. A61C 13/28
[52] U.S. Cl. ...................................... 433/169; 433/173
[58] Field of Search ................. 433/169, 173, 174, 175

[56] References Cited
U.S. PATENT DOCUMENTS

| | | | |
|---|---|---|---|
| 2,880,508 | 4/1959 | Lester et al. | 433/169 |
| 3,497,953 | 3/1970 | Weissman | 433/173 |
| 3,722,094 | 3/1973 | Rivoir | 433/173 |
| 3,863,344 | 2/1975 | Pillet | 433/169 |
| 3,955,280 | 5/1976 | Sneer | 433/173 |
| 4,215,986 | 8/1980 | Riess | 433/173 |
| 4,220,712 | 9/1980 | Staffolani | 433/173 |
| 4,552,532 | 11/1985 | Mozsary | 433/173 |
| 4,622,010 | 11/1986 | Koch | 433/173 |
| 4,746,293 | 5/1988 | Lundgren et al. | 433/173 |

FOREIGN PATENT DOCUMENTS

| | | | |
|---|---|---|---|
| 0131831 | 1/1985 | European Pat. Off. | 433/173 |
| 2247649 | 4/1973 | Fed. Rep. of Germany | 433/173 |
| 2413883 | 9/1975 | Fed. Rep. of Germany | 433/173 |
| 2419080 | 11/1975 | Fed. Rep. of Germany | 433/173 |
| 2704390 | 8/1978 | Fed. Rep. of Germany | 433/173 |
| 2733394 | 2/1979 | Fed. Rep. of Germany | 433/173 |
| 2824118 | 12/1979 | Fed. Rep. of Germany | 433/173 |
| 2824214 | 12/1979 | Fed. Rep. of Germany | 433/173 |
| 3043336 | 6/1981 | Fed. Rep. of Germany | 433/173 |
| 3300764 | 7/1984 | Fed. Rep. of Germany | 433/173 |
| 86/01393 | 3/1986 | PCT Int'l Appl. | 433/221 |
| 1586729 | 3/1981 | United Kingdom | 433/173 |

Primary Examiner—John J. Wilson
Attorney, Agent, or Firm—Foley & Lardner, Schwartz, Jeffery, Schwaab, Mack, Blumenthal & Evans

[57] ABSTRACT

A tooth-root implant of high fatigue strength, intended for a two-stage implantation technique, comprises a sleeve (1) which, in its inner region, has retention means (6b), on which a pressure plate (2a) rests loosely. An insertable superstructure bearing (3) is arranged on the pressure plate (2a) and is surrounded, at least partially, by a plastic casing (4). A screw plug (5) is also provided which closes off the upper part of the sleeve (1) in such a way that positive contact is made.

32 Claims, 4 Drawing Sheets

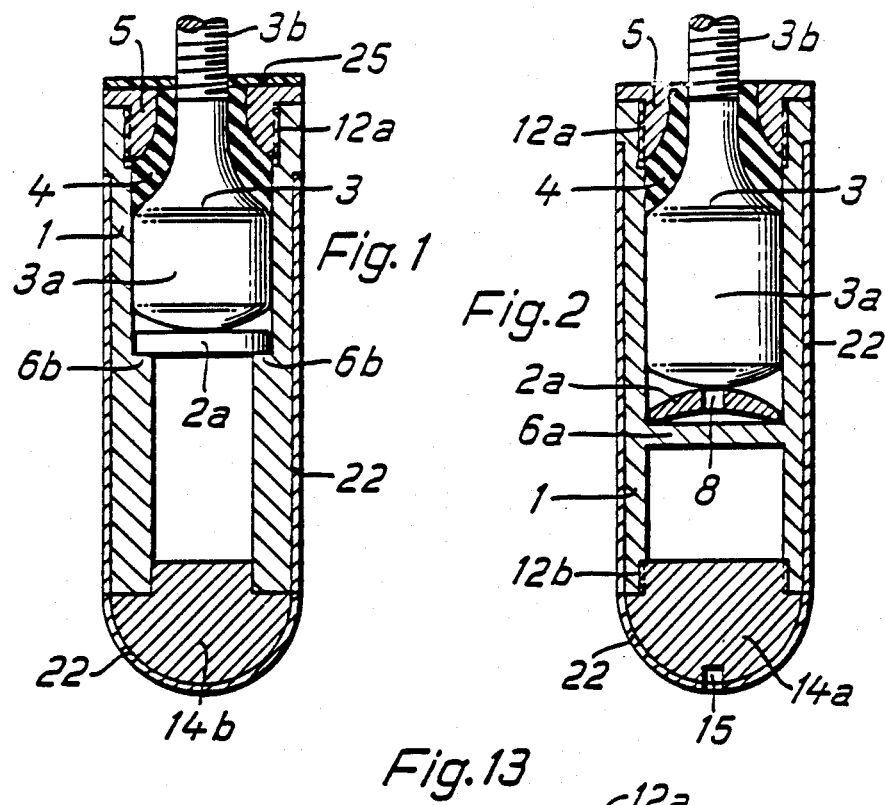
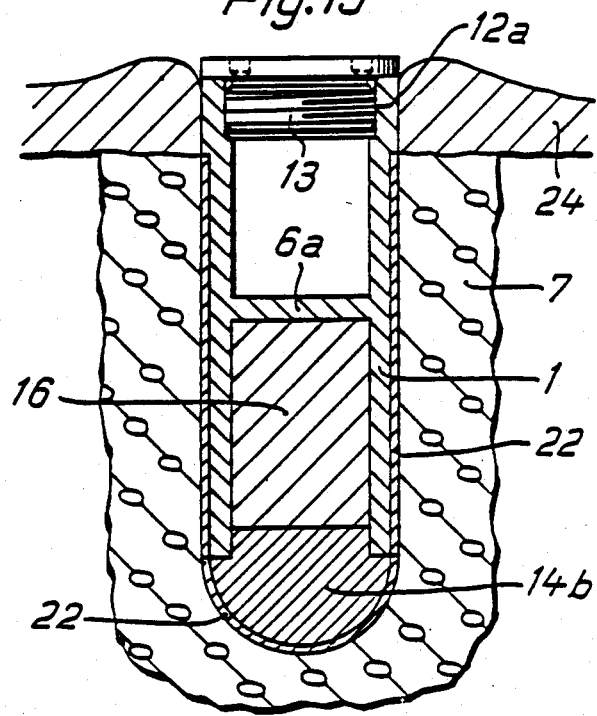

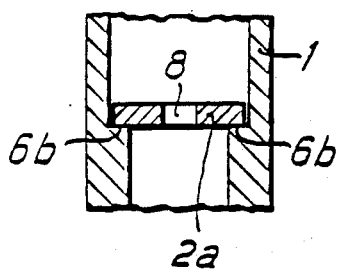
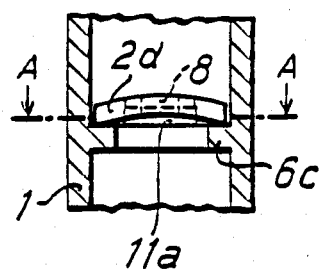
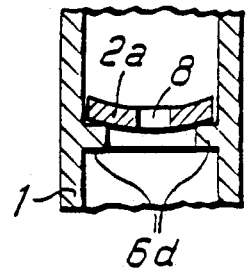
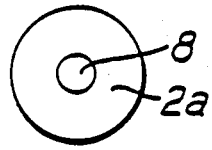
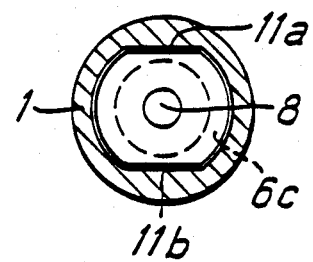
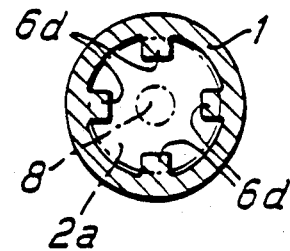
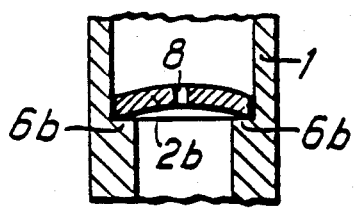
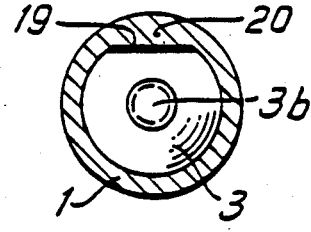
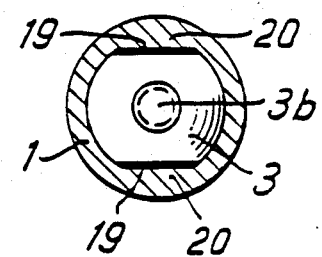
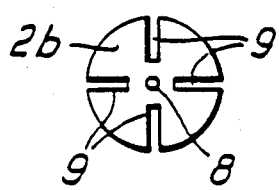
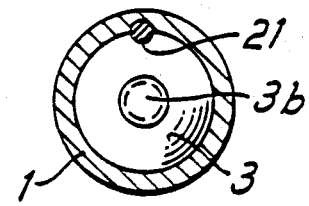
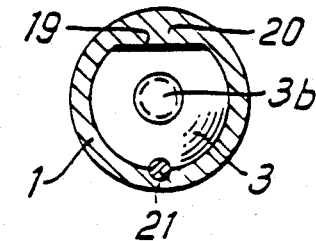

TOOTH-ROOT IMPLANT WITH LONG-TERM RESISTANCE TO REPETITIVE STRESSES

BACKGROUND OF THE INVENTION

The invention relates to a tooth-root implant of high fatigue strength which is anchored in the jawbone and which has the ability of receiving a superstructure.

Natural teeth are connected to the jawbone by means of the parodontium. Because of the elasticity of the fibrous structure of the tooth-holding member, the tooth is not anchored rigidly in the jawbone, but is suspended elastically. This so-called physiological movability of the teeth varies from species to species. In humans, it amounts to approximately 30 $\mu$m, that is to say under maximum chewing pressure the tooth is pressed approximately 30 $\mu$m into the socket. At the same time, because of the special arrangement of the fibers in the parodontium, most of the jawbone surrounding the tooth socket is subjected not to compressive stress, but to tensile stress. The tooth-root implants which have become known hitherto cannot simulate the function of the parodontium to a sufficient extent. Since tooth-root implants are used, in many cases, for anchoring bridges, the second pier of which is still a natural tooth, it is necessary not to fasten the superstructure rigidly to the root implant, but to ensure the mobility between the superstructure and implant which a natural tooth possesses in relation to the jawbone.

Non-physiological moments of force occuring during the chewing process at the interface between the implant and bone bed are avoided in this way. A movable forcetransmitting structure between the superstructure and implant must also be designed so that load peaks during the chewing process are absorbed and transferred to the bed only in a damped state, because, in a natural tooth, the parodontium also performs the function of a "shock absorber".

A device for absorbing such pressure peaks is known from German Offenlegungsschrift 2,733,394. This describes a damping element in which a pin connected to the core of the tooth root projects into a metal sleeve with elastic plastic.

There are also known superstructures in which a crown is fastened elastically to the root in such a way that a cavity filled with elastomer is formed between a plug connected to the root and the crown; see German Offenlegungsschrift 2,247,649. A shock-absorbing arrangement which does without the insertion of elastic intermediate pieces or layers is described in German Offenlegungsschrift 2,830,025. Here, damping is brought about by a tapping piece receiving the superstructure and having a tilting support which terminates in the form of a lip and which rests sealingly on the outer edge of an intermediate piece.

A further damping member made of physiologically harmless polymers with a modulus of elasticity of between 1,000 and 5000 N/mm$^2$ is described in German Offenlegungsschrift 2,824,214. The damping members which have existed or become known hitherto consist essentially of plastics, such as, for example, polyacrylate, polypropylene, polysultone or polymethacrylate; see German Offenlegungsschrift 2,419,080, German Offenlegungsschrift 3,043,336, German Auslegesschrift 2,413,883, German Offenlengungsschrift 2,704,390 and German Offenlegungsschrift 2,824,118.

In general, although plastics initially posses a modulus of elasticity suitable for damping purposes, nevertheless this and other mechanical properties undergo a detrimental change as a result of the continuous stress exerted during the chewing process. Plastics experience fatigue very quickly after a certain number of load alternations, so that the damping elements have to be exchanged even after only relatively short periods of time or after a small number of load alternations. U.S. Pat. No. 3,722,094 allows for this disadvantage by inserting a helical spring as a damping element between the superstructure and tooth root. However, an essential disadvantage of the arrangement, in addition to its constructive inadequacies, is that, under pressure load, a gap can form between the superstructure and the tooth root implant. Saliva and food residues can then penetrate into the cavity receiving the helical spring. Serious medical and hygienic problems arise as a result.

SUMMARY OF THE INVENTION

The object of the present invention is, therefore, to provide a constructively simple, but medically highly effective tooth-root implant which does not have the disadvantages of the known implants and which does not show any signs of loosening in the bony implant bed even after a long period of continuous load. A further part object is to provide a tooth-root implant for a two-stage implantation, in which bacteria causing infection are effectively prevented from penetrating into the region of the bony implant bed and of the root implant itself.

According to the invention, in a tooth-root implant, the object is achieved in that it is designed as a sleeve containing a pressure which serves as a damping diaphragm and on which rests a superstructure bearing surrounded, at least partially, by a plastic casing, and in that a screw plug is provided which closes off the upper part of the sleeve in such a way that a positive contact, preferably under pressure, is made with the plastic casing. At the same time the sleeve, in its inner region, can have retention means for supporting the pressure plate. These retention means can be designed as a slope extending continuously round or as pointing inwards radial lugs or as a cylindrical thickened zone within the sleeve. It is also possible for the retention means to be an intermediate diaphragm hermetically separating the sleeve into an upper region pointing towards the superstructure and a lower region pointing towards the bony implant bed. It is expedient, at the same time, if the pressure plate rests loosely on the retention means. The retention means itself or themselves can be arranged in a position within the region between the upper third and the lower fifth of the sleeve. The pressure plate is designed as a round disc which can preferably be provided with a central perforation. It is possible for the pressure plate additionally to have an annular bead in its edge region, approximately in the manner of a bowl rim. So that optimum damping moments can be set individually, the pressure plate can have a plurality of slots which extend from the periphery of the pressure plate towards its center, without reaching the central region of the pressure plate itself, this central region being provided with a central perforation if appropriate. It is also possible for the pressure plate to be designed not as a round disc, but in a form in which at least one plate segment in the form of a portion of a circle has been cut off from the initial round disc. To obtain a more accurate setting of the optimum vibration-damping conditions, it may be expedient to design the pressure plate in such a way that it has a variable cross-sectional thickness profile. The geometry of the upper side and/or lower side of the pressure plate can have a plane or spherical or aspherical form.

The superstructure bearing has a cylindrical cross-sectional geometry in its base region, and, in its region pointing towards the superstructure, it is made bar-shaped or bottleneck-shaped, at least the last-mentioned region being equipped with a plastic casing. It is expedient, at the same time, that the base region of the superstructure bearing is retained positively in the upper inner space of the sleeve. The upwardly narrowing region of the superstructure bearing is designed as a threaded neck for the releasable fastening of the superstructure. In order to perform a two-stage implantation technique the sleeve, in its upper region, has an internal thread for temporarily receiving a sleeve plug. The part of the sleeve pointing towards the bony implant bed can have an insertable closing-off part which preferably has at least one recess for the insertion of a screwing tool (hexagon-socket wrench). The closing-off part can also be retained in the sleeve without a thread by means of a press fit. On the other hand, it is also possible to provide the closing-off part with a thread which matches a corresponding internal thread in the lower sleeve part. Furthermore, to make it easier to screw in the closing-off part, a recess for engaging a hexagon-socket wrench can be provided. The closing-off part expediently has a rounded outer contour. The sleeve, which has an intermediate diaphragm in its inner region, can be filled with an elastic plastic material in its lower region. It is also possible for this lower region to have a prestressed helical spring which rests against the underside of the intermediate diaphragm at one end and against the closing-off part at the other end. Instead of a helical spring, a prestressed flexural bar can also be provided. It is expedient to design the tooth-root implant according to the invention in such a way that the superstructure bearing has at least one flattened surface as a rotation prevention means, which matches a corresponding thickened zone in the inner region of the upper part of the sleeve. Furthermore, it is also possible to provide a stud guide or rail guide extending along the inner wall of the sleeve parallel to its vertical axis and which corresponds to a recess in the super-structure bearing, as a rotation prevention means for the superstructure bearing.

According to an especially advantageous embodiment of the present invention, the sleeve, the screw plug and, if appropriate, the closing-off part can be composed of metallic material compatible with the human body, preferably of titanium or a titanium alloy. The pressure plate and the superstructure bearing are expediently composed of high fatigue-strength metal, preferably spring steel. According to a preferred embodiment of the present invention, the sleeve and the closing-off part have a partial or complete coating of bioactive material. This material can be a composite material which has been produced by isostatic or hot-isostatic pressing of an inorganic bioactive starting material and of a metal powder compatible with the human body, preferably a titanium or titanium alloy powder. It is also possible, however, for the sleeve or the closing-off part to have, in discrete surface regions, inclusions of bioactivated composite materials obtained by isostatic or hot-isostatic pressing, the non-positive and positive anchoring of the individual composite bodies being carried out, with hot-isostatic pressing once again taking place at the same time. The surface geometries with these discrete inclusions can be highly diverse; preferably, however, the inclusions will be circular. The tooth-root implant according to the invention can be used for receiving a superstructure or can be provided as an individual pier for anchoring dental-prosthetic bridge structures.

BRIEF DESCRIPTION OF THE DRAWINGS

The invention is explained below with reference to diagrammatic drawings. In these:

FIG. 1 shows a first embodiment of the tooth-root implant with a loose plane pressure plate;

FIG. 2 shows a second embodiment of the tooth-root implant with an intermediate diaphragm, on which a pressure plate rests;

FIG. 7a shows a cut-out representation of a further embodiment of a tooth-root implant sleeve with an inner cylindrical thickened zone;

FIG. 7b shows a plan view of the circular pressure plate shown in FIG. 7a;

FIG. 8a shows a further alternative form of the tooth-root implant sleeve with a slope 6c extending continuously round on its inside;

FIG. 8b shows a section along the line A—A FIG. 8a;

FIG. 9a shows a further alternative form of a tooth-root implant sleeve with radial lugs provided inside it as retention means for the pressure plate;

FIG. 9b shows a plan view of the pressure plate illustrated in FIG. 9a, with four retention means (radial lugs);

FIG. 10a shows a cut-out representation of a sleeve according to FIG. 7a, but with another form of pressure plate;

FIG. 10b shows a plan view of the pressure plate illustrated in FIG. 10a, with slots and a central perforation;

FIG. 11a shows a cross-section through a tooth-root implant sleeve which has, in the inner region of the sleeve, a plane finished zone which matches a corresponding flattened surface of the superstructure bearing;

FIG. 11b shows that which is illustrated in FIG. 11a, but with symmetrically arranged thickened zones and flattened surfaces;

FIG. 12a shows a section through a tooth-root implant sleeve with a stud guide as a rotation prevention means in the inner region of the sleeve;

FIG. 12b shows a combination of that which is shown in FIGS. 11a and 12a;

FIG. 13 shows a tooth-root implant in situ with a temporary sleeve plug (the first phase of a two-stage implantation technique);

DETAILED DESCRIPTION OF THE PREFERRED EMBODIMENTS

Figure 3:
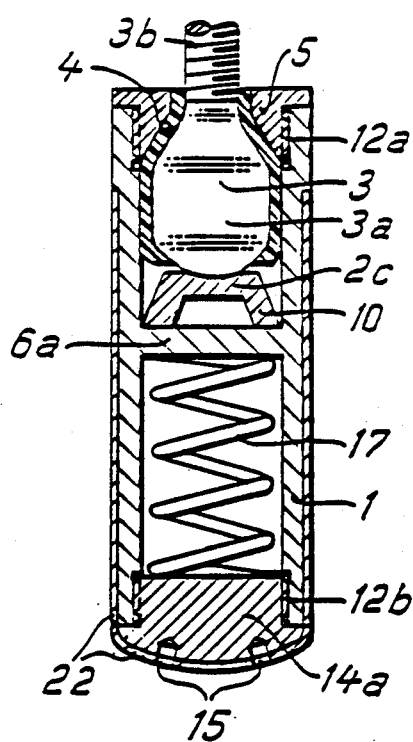
FIG. 3 shows a third embodiment of the tooth-root implant with an intermediate diaphragm supported in the lower region by means of a spring.

FIG. 1 shows a tooth-root implant formed from a metal sleeve 1 containing, in its inner region, a pressure plate which is designed as a plane-parallel round disc 2a in the example illustrated. The pressure plate rests freely on a cylindrical thickened zone 6b within the sleeve 1. On the pressure plate 2a rests a superstructure bearing 3 which comprises a cylindrical base region 3a and a bar-shaped or bottlenecked-shaped region 3b, the part 3b having a thread for receiving a superstructure (not shown). In FIG. 1, the superstructure bearing 3 has a plastic casing 4 in the region of its upper part. A screw plug 5 closes off the tooth-root implant. This plug 5 is shaped so that it rests over the entire surface against the plastic casing 4. At the same time, it is desirable for a certain pressing force to be exerted on the plastic casing 4. The sleeve is closed in its lower part by an insertable closing-off part 14b. Both the sleeve and the closing-off part 14b can have a partial or complete coating of bioactive material 22. The screw plug 5 carries a thread which matches a corresponding internal thread 12a in the upper region of the sleeve 1. A sealing ring 25 made of elastic material is also arranged above the screw plug 5. The superstructure bearing 3, in its region pointing towards the pressure plate 2a, is designed in such a way that it has only a small surface of contact with the pressure plate 2a, preferably only point contact.

In FIG. 2, the sleeve 1, in its inner region, has a retention means which is designed as an intermediate diaphragm 6a and which closes off the sleeve 1 hermetically into a upper region and a lower region. A pressure plate 2a of a different shape rests on this intermediate diaphragm 6a, once again so as to be freely movable, and has a central perforation 8 for receiving the superstructure 3 in the manner of a trough. In this illustration, the closing-off part 14a is provided with a thread which matches an internal thread 12b in the lower region of the sleeve 1. A recess 15 is also provided for a screwing tool. The superstructure bearing 5 can be shaped according to individual circumstances but there must always be a cylindrical region 3a which rests positively against the inner wall of the sleeve 1. In the same way, the narrowing region 3b of the super-structure bearing 3a can have a differing form; however, here too, the space between the narrowing region 3b and the upper part of the sleeve 1 or the conical part of the screw plug 5 must always be filled completely with the plastic casing 4.

FIG. 3 illustrates a further alternative form, in which the intermediate diaphragm 6a is supported elastically by means of a helical spring 17 which, under prestress, fills the lower sleeve region between the screw-in closing-off part 14a and the underside of the intermediate diaphragm 6a. The pressure plate shown is a pot shaped pressure plate 2c with an annular bead 10. The superstructure bearing 3 rests in a trough-shaped depression and is provided completely with a plastic casing 4, with the exception of the region resting on the pressure plate plate 2c.

Figure 4:
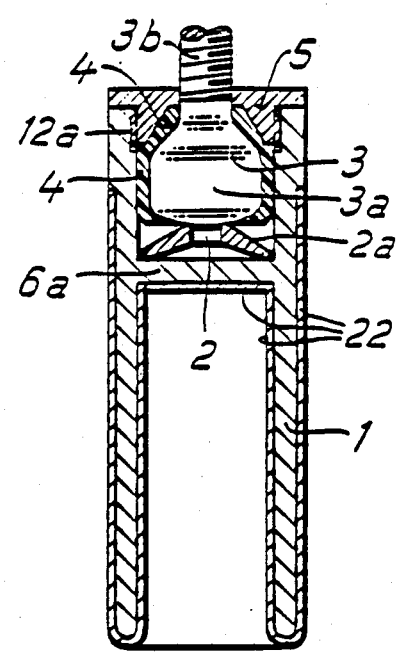
FIG. 4 show a fourth embodiment of the tooth-root implant with a sleeve shape open towards the bony implants bed.

FIG. 4 shows a further tooth-root implant sleeve 1. It is designed as an open sleeve 1 in the region pointing towards the bony implant bed 7, and it is provided, on its inner wall too, with a coating composed of a bioactive material 22. A pressure plate 2a with a central perforation 2 rests on the intermediate diaphragm 6a. It must be stressed that the retention means 6a–6d can be attached at differing heights within the sleeve 1; see, for example, the corresponding arrangement in FIG. 2 (the lower region of the sleeve) and in FIG. 4 (the upper region of the sleeve).

Figure 5:
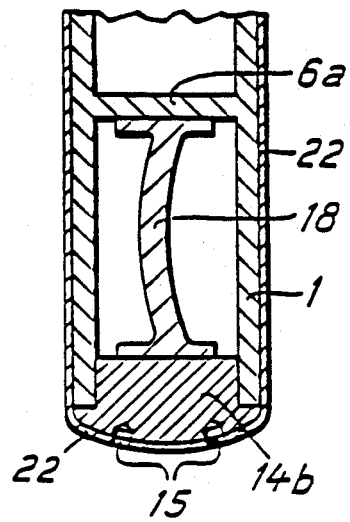
FIG. 5 shows a cut-out representation of a fifth embodiment of a tooth-root implant with a flexural bar as a support for the intermediate diaphragms.

FIG. 5 shows a cut-out representation of a further alternative form of a supporting structure for the intermediate diaphragm 6a, specifically a prestressed flexural bar 18. There is, of course, a variety of other possible constructions.

Figure 6:
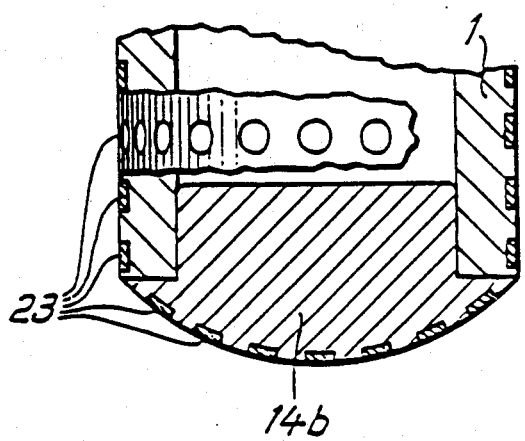
FIG. 6 shows a detailed representation of a lower part of a tooth-root implant with a multiplicity of inclusions of bioactive particles.

The detailed representation in FIG. 6 illustrates that partial inclusion of prefabricated inclusion bodies 23 composed of bioactive material in the surface region of the sleeve 1 and of the closing-off part 14b. These inclusions 23 can be composed, for example, of a composite material produced from a metallic component and at least on bioactive material by means of an isostatic pressing process. The bioactive inclusions 23 prefabricated in this way can be inserted with an exact fit to the recesses of corresponding shape and then subjected to a further isostatic pressing operation, thus obtaining a firm "weld" in the recesses provided for them. As a result of this technique, the tooth-root implant sleeve 1 produced from biologically inert metallic material is, as it were, subsequently "bioactivated".

The geometrical shape of the pressure plate and the constructive design of the retention means in the inner region of the sleeve 1 can take many forms. In FIG. 7a the pressure plate is shown as a plane-parallel round disc 2a with a central perforation 8; see also the corresponding plan view in FIG. 7b.

As shown in FIG. 8a, the retention means can also be designed as a slope 6c which extends continuously round and on which a pressure plate 2d with a central perforation 8 is supported; see the section along the line A—A shown in FIG. 8b. FIG. 9a, instead of a slope extending continuously round, radial lugs 6d are arranged in the inner region of the sleeve 1 and guarantee a secure support for the pressure plate 2a which, in this case, is designed as a sagged disc.

The pressure plate can also be provided with several slots 9 which are arranged peripherally and which extend in the direction of the plate center. A controlled setting of the cushioning capacity of the pressure plate 2b can be achieved thereby. The pressure plate can also be produced from a round disc 2a (see FIG. 7b) in a modified form in which, for example, two plate segments 11a, 11b in the form of a portion of a circle are detached from it; see FIG. 8b. Various other trimmings are possible.

FIG. 11a shows a section through a particular embodiment of a tooth-root implant sleeve 1, a thickened zone 20 extending parallel to the sleeve axis being provided in the inner region of the sleeve 1. Correspondingly, the super-structure bearing 3 to be inserted has a flattened surface 19 in its cylindrical base region 3a. This guarantees a means of preventing rotation. This is especially advantageous because the device according to the invention is designed in such a way that not only the superstructure, but also the superstructure bearing 3 and the pressure plate 2a–2d are retained in an exchangeable manner. As shown in FIG. 11b, several thickened zones 20 in the inner region of the sleeve 1 and several flattened surfaces on the super-structure bearing 3 can also be provided. Finally, it is also possible to arrange parallel to the sleeve axis, in the inner region of the sleeve 1, a stud guide or rail guide 21 which matches a corresponding longitudinal groove in the base region 3a of the superstructure bearing 3. FIG. 12b shows a combination of the two proposed solutions (FIG. 11a and FIG. 12a).

FIG. 13 shows a tooth-root implant anchored in the implant bed 7. A coating composed of bioactive material is applied over the entire region of the outer shell of the sleeve 1 and of the closing-off part 14b. In the region of the gum 24, the sleeve made of metal compatible with the human body rests directly against the body tissue. A plastic material 16 filling the lower sleeve region completely is inserted as an elastic cushioning body underneath the intermediate diaphragm 6a. In order to perform a two-stage implantation technique, the tooth-root implant is implanted, initially without a superstructure bearing and pressure plate, and is then equipped with a sleeve plug 13. After the settling-in or rooting-in phase, the sleeve plug 13 is removed again, the pressure plate, superstructure bearing and screw plug are fitted, the sealing ring 25 is attached, and finally the actual superstructure is fastened in the upper region 3b of the superstructure bearing 3. The second phase of the two-stage implantation process is thus concluded. The constructive design guarantees that no cavities, into which saliva could otherwise penetrate, form in the upper region of the tooth-root implant. The plastic casing 4 surrounding the superstructure bearing 3 essentially performs sealing functions and does not serve, as in many other tooth-root implants, to transmit the chewing forces occuring in the vertical direction during chewing. Here, these forces are initially absorbed by the pressure plate, by means of which they are damped and then transferred to the jaw bone via the outer casing of the implant. These transfers of force prevent tooth-root implants from luxation and working loose. Adverse irritant effects on the bone are eliminated, and the repulsion effect occuring as a defence reaction under load is avoided. The superstructure bearing 3, especially in its upper region 3b, can absorb and transfer the transverse forces occuring during chewing, so that the surrounding plastic casing 4 does not have to perform the function of the main damping of the forces.

Figure 14:
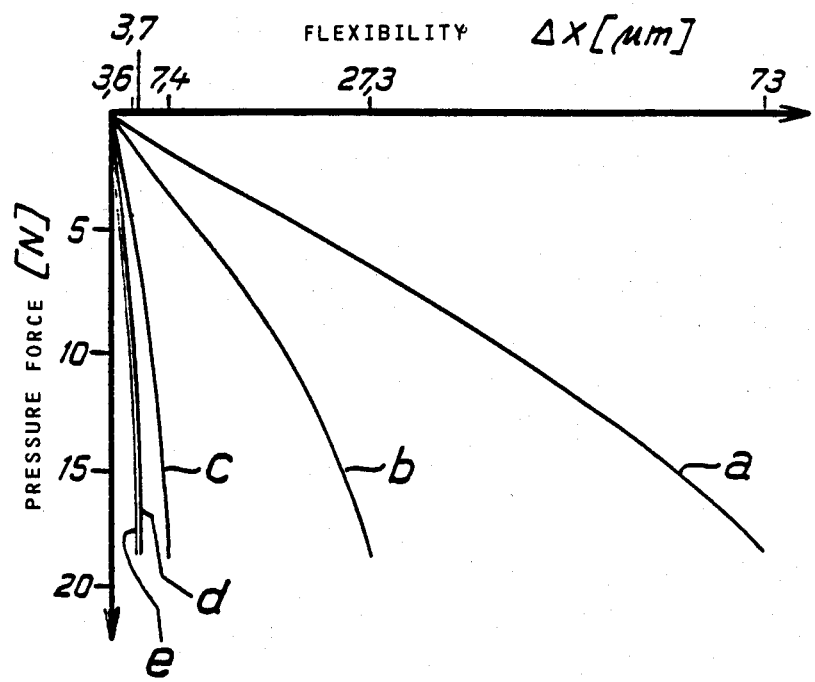
FIG. 14 shows a graphical representation of the flexibility of five plane-parallel pressure plates of differing plate thickness as a function of the pressure force.

The fact that the tooth-root implant according to the invention cannot perform its function fully without the loosely inserted pressure plate 2a–2d is of particular importance; the presence of this loosely resting pressure plate is therefore an essential feature. Measurements on model implants of this type have shown that pressure plates resting freely on a retention means are the most suitable for absorbing and transferring presure peak loads. FIG. 14 illustrates graphically plane-parallel round discs 2a of differing thickness in terms of their flexibility when specific pressure forces are exerted. A round disc 2a of diameter of between 2.5–2.8 mm exhibits the following flexibility $\Delta$ x as a function of the particular plate thickness:

| Reference symbol | Plate thickness (mm) | $\Delta \times$ ($\mu$m) |
| --- | --- | --- |
| a | 0.1 | 73 |
| b | 0.2 | 27.3 |
| c | 0.3 | 7.4 |
| d | 0.4 | 3.7 |
| e | 0.5 | 3.6 |

It should be emphasized that, depending on the region of use of the implant, various deliberate changes to the properties of the pressure plate can be made by means of the different structuring, thickness, slots, etc. which have been described.

What is claimed is:

1. A tooth-root implant of high fatigue strength, comprising;
    a sleeve having a coating of a bioactive material;
    a pressure plate situated within said sleeve which serves as a damping diaphragm and on which rests a superstructure bearing surrounded, at least partially, by a plastic casing, and wherein a screw plug is provided with closes off an upper part of the sleeve in such a way that positive contact is made with the plastic casing; and
    retention means for supporting said pressure plate, said pressure plate resting loosely on said retention means; wherein
    said pressure plate and said superstructure bearing are composed of high fatigue-strength metal.

2. An implant as claimed in claim 1, wherein said retention means is situated in an inner region of the sleeve in order to support the pressure plate.

3. An implant as claimed in claim 2, wherein the retention means is designed as a slope extending continuously in a circumferential manner.

4. An implant as claimed in claim 2, wherein the retention means comprises as least three radial lugs pointing inwards.

5. An implant as claimed in claim 2, wherein the retention means is the upper part of a cylindrical thickened zone within the sleeve.

6. An implant as claimed in claim 1 wherein the retention means is an intermediate diaphragm hermetically separating the sleeve into an upper region pointing towards the superstructure and a lower region pointing towards the bony implant bed.

7. An implant as claimed in claim 6 wherein the lower region of the sleeve is filled with an elastic plastic material.

8. An implant as claimed in claim 6 wherein the lower region has a prestressed helical spring which rests against the underside of the intermediate diaphragm at one end and against the closing-off part at the other end.

9. An implant as claimed in claim 8, wherein, instead of the helical spring, a prestressed flexural bar is provided.

10. An implant as claimed in claim 1 wherein the retention means for the pressure plate is arranged in a position within the region between the upper third and the lower fifth of the sleeve.

11. An implant as claimed in claim 1, wherein the pressure plate is designed as a round disc with a central perforation.

12. An implant as claimed in claim 11, wherein the pressure plate is configured as the round disc (2a) which additionally has an annular bead in its edge region.

13. An implant as claimed in claim 11, wherein the pressure plate has a plurality of slots which extend from the periphery of the pressure plate towards its center, without reaching the central region of the pressure plate itself, this central region being provided with a central perforation.

14. An implant as claimed in claim 1 wherein the pressure plate is formed by removing at least one plate segment in the form of a portion of a circle.

15. An implant as claimed in claim 1 wherein the pressure plate has a variable cross-sectional thickness profile.

16. An implant as claimed in claim 1 wherein the upper side and lower side of the pressure plate each has a plane, spherical, or aspherical form.

17. An implant as claimed in claim 1, wherein the superstructure bearing has a cylindrical cross-sectional geometry in its base region and is either bar-shaped or bottlenecked-shaped in its region pointing toward the superstructure, at least the last-mentioned region being equipped with a plastic casing.

18. An implant as claimed in claim 17, wherein the base region of the superstructure bearing is retained positively in the upper inner space of the sleeve.

19. An implant as claimed in claim 17 wherein an upwardly narrowing region of the superstructure bearing is designed as a threaded neck for the releasable fastening of the superstructure.

20. An implant as claimed in claim 1, wherein, in order to perform a two-stage implantation technique, the sleeve in its upper region, has an internal thread for temporarily receiving a sleeve plug.

21. An implant as claimed in claim 1, wherein a part of the sleeve pointing towards the bony implant bed has an insertable closing-off part which preferably has at least one recess for the insertion of a hexagon-socket wrench.

22. An implant as claimed in claim 21, wherein the closing-off part is retained in the sleeve by means of a press fit.

23. An implant as claimed in claimed 21, wherein the closing-off part has a thread which matches a corresponding internal thread in the lower sleeve part, and also contains at least one recess for engaging a hexagon-socket wrench.

24. An implant as claimed in one of claim 21 wherein the closing-off part has a rounded outer contour.

25. An implant as claimed in claim 21, wherein the sleeve and the closing-off part have a partial or complete coating of bioactive material.

26. An implant as claimed in claim 25, wherein the bioactive material is a composite material which has been produced by isostatic, preferably hot-isostatic pressing of an inorganic bioactive starting material and of a metal powder compatible with the human body, preferably a titanium or titanium alloy powder.

27. An implant as claimed in claim 25 wherein the sleeve and/or the closing-off part have, in discrete surface regions, inclusions of bioactivated composite materials obtained by isostatic or hot-isostatic pressing, the non-positive and positive anchoring of the individual composite bodies being carried out, with hot-isostatic pressing once again taking place at the same time.

28. An implant as claimed in claim 1, wherein, as seen in plan view, the superstructure bearing has at least one flattened surface as a rotation prevention means, which matches a corresponding thickened zone in the inner region of the sleeve.

29. An implant as claimed in claim 1 wherein a stud guide or rail guide extending along the inner wall of the sleeve parallel to its vertical axis and matching a corresponding recess in the superstructure bearing is provided as a rotation prevention means for the superstructure bearing.

30. A use of the implant as claimed in claim 1 as a tooth-root implant for receiving a superstructure or as an individual pier for anchoring dental-prosthetic bridge structures.

31. An implant as claimed in claim 1, wherein said positive contact with said plastic casing is made under pressure.

32. An implant as claimed in claim 1, wherein said high fatigue-strength metal is spring steel.

* * * * *